(12) United States Patent
Norton et al.

(10) Patent No.: US 9,295,645 B2
(45) Date of Patent: Mar. 29, 2016

(54) COMPOSITIONS COMPRISING BUPRENORPHINE

(75) Inventors: Richard L. Norton, Fort Collins, CO (US); Mingxing Zhou, Fort Collins, CO (US)

(73) Assignee: Indivior UK Limited, Slough (GB)

( * ) Notice: Subject to any disclaimer, the term of this patent is extended or adjusted under 35 U.S.C. 154(b) by 102 days.

(21) Appl. No.: 13/703,015

(22) PCT Filed: Jun. 6, 2011

(86) PCT No.: PCT/GB2011/051058
§ 371 (c)(1),
(2), (4) Date: Feb. 5, 2013

(87) PCT Pub. No.: WO2011/154725
PCT Pub. Date: Dec. 15, 2011

(65) Prior Publication Data
US 2013/0202658 A1 Aug. 8, 2013

(30) Foreign Application Priority Data
Jun. 8, 2010 (GB) .................................. 1009546.1

(51) Int. Cl.
*A61K 9/10* (2006.01)
*A61K 9/00* (2006.01)
*A61K 31/485* (2006.01)
*A61K 47/10* (2006.01)
*A61K 47/26* (2006.01)
*A61K 31/439* (2006.01)

(52) U.S. Cl.
CPC ................. *A61K 9/10* (2013.01); *A61K 9/0019* (2013.01); *A61K 31/439* (2013.01); *A61K 31/485* (2013.01); *A61K 47/10* (2013.01); *A61K 47/26* (2013.01)

(58) Field of Classification Search
CPC ..... A61K 9/0019; A61K 9/10; A61K 31/439; A61K 31/485; A61K 47/10; A61K 47/26
See application file for complete search history.

(56) References Cited

U.S. PATENT DOCUMENTS

| | | | |
|---|---|---|---|
| 4,599,354 A | 7/1986 | Shulman | |
| 5,346,903 A | 9/1994 | Ackerman | |
| 5,486,362 A | 1/1996 | Kitchell | |
| 7,041,320 B1 | 5/2006 | Nuwayser | |
| 2003/0211157 A1 | 11/2003 | Simon | |
| 2004/0151670 A1 * | 8/2004 | Blondino et al. | 424/45 |
| 2005/0048115 A1 | 3/2005 | Mangena | |
| 2009/0061011 A1 * | 3/2009 | Talton | 424/501 |

FOREIGN PATENT DOCUMENTS

| | | | |
|---|---|---|---|
| GB | 784659 | * | 10/1957 |
| WO | 01/15699 A1 | | 3/2001 |
| WO | 2007103185 A2 | | 9/2007 |

OTHER PUBLICATIONS

Lindhardt et al "Intranasl absorption of buprenorphine-in vivo bioavailability study in sheep", Int. J. of Pharm.; 205, (2000) p. 159-163.*
International Search Report and Written Opinion mailed May 10, 2012 for priority application PCT/GB2011/051058.
Search Report dated Oct. 6, 2010 for priority application GB1009546.1.
International Preliminary Report on Patentability mailed Dec. 20, 2012 for priority application PCT/GB2011/051058.

* cited by examiner

*Primary Examiner* — Robert A Wax
*Assistant Examiner* — Melissa Mercier
(74) *Attorney, Agent, or Firm* — Mintz Levin Cohn Ferris Glovsky and Popeo, P.C.

(57) ABSTRACT

This disclosure relates to a buprenorphine sustained release delivery system for treatment of conditions ameliorated by buprenorphine compounds. The sustained release delivery system includes a flowable composition containing a suspension of buprenorphine, a metabolite, or a prodrug thereof.

20 Claims, 4 Drawing Sheets

COMPOSITIONS COMPRISING BUPRENORPHINE

CROSS-REFERENCE TO RELATED APPLICATIONS

This application is a US National Stage of International Application No. PCT/GB2011/051058, filed 6 Jun. 2011, which claims the benefit of GB 1009546.1, filed 8 Jun. 2010, both herein fully incorporated by reference.

FIELD OF THE INVENTION

This disclosure relates to a buprenorphine sustained release delivery system for treatment of conditions ameliorated by buprenorphine compounds. The sustained release delivery system includes a flowable composition containing a suspension of buprenorphine, a metabolite, or a prodrug thereof.

BACKGROUND OF THE INVENTION

Buprenorphine (also known as (2S)-2-[(−)-(5R,6R,7R,14S)-9α-cyclo-propyl-methyl-4,5-epoxy-6,14-ethano-3-hydroxy-6-methoxymorphinan-7-yl]-3,3-di-methylbutan-2-ol and marketed under the trade names SUBUTEX™ and SUBOXONE™ for relief of opioid addiction.

The chemical structure of buprenorphine is shown in formula (1).

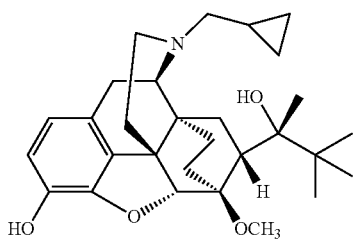

Formula (1)

Buprenorphine is most often used to treat symptoms arising from opioid addiction and for the long term relief of pain. Currently, the commercial opioid addiction products are SUBUTEX™ and SUBOXONE™ marketed by RB Pharma Inc. These products are in a tablet formulation and are intended to deliver therapeutic levels of buprenorphine for short periods of time of up to several hours and are typically taken either buccally or sub-lungually. However, the patient is required to supplement this dose at regular intervals, and there are often issues with diversion in patients with an opioid dependence problem. There is a need therefore for a longer term, non-divertible method of administering buprenorphine which delivers a constant and effective dose of the active to the patient over a period of up to 30 days, and which does not result in an unwanted accumulation of residual active in the patient's metabolism.

Various sustained release methods are employed in the pharmaceutical industry, for example, systems such as solid, biodegradable rods, or nondegradable reservoirs. These, however, typically require surgical implantation and furthermore, for the nondegradable delivery systems, a second surgical procedure is required to remove the empty reservoir.

There is a continuing need to develop products providing increased bioavailability of buprenorphine. In particular, there is a need to develop sustained release formulations of buprenorphine that do not suffer from low bioavailability, poor release kinetics, injection site toxicity, relatively large volume injections, and inconveniently short duration of release.

SUMMARY OF THE INVENTION

The present invention is directed to a buprenorphine sustained release delivery system capable of delivering buprenorphine, a metabolite, or a prodrug thereof for a duration of about 7 days to about 1 month. The buprenorphine sustained release delivery system includes a flowable composition for the sustained release of buprenorphine, a metabolite, or a prodrug thereof. The buprenorphine sustained release delivery system provides at least 7 days and up to 30 days release profiles characterized by an exceptionally high bioavailability and minimal risk of permanent tissue damage and typically no risk of muscle necrosis.

Surprisingly, it has been found that such a sustained release delivery system is achieved by a composition comprising a suspension of buprenorphine in water, wherein the buprenorphine is in particulate form.

Accordingly, there is provided according to the first embodiment of the present invention, a composition comprising:
 a suspension of 5-20 wt % of buprenorphine in water; and,
 a polyethylene glycol (PEG) polymer,
wherein:
 the buprenorphine is in particulate form with an average particle size of less than 200µ; and,
 the composition does not comprise a polylactide or polyglycolide polymer or mixture thereof.

Preferably, the average particle size of the buprenorphine in the composition as hereinbefore described is less than 150µ, preferably less than 120µ, preferably less than 100µ, preferably less than 80µ, preferably less than 60µ, preferably less than 50µ, preferably less than 40µ.

Especially preferably, the average particle size of the buprenorphine in the composition as hereinbefore described is less than 20µ, more especially preferably less than 10µ.

In one preferred embodiment, the composition as hereinbefore described comprises buprenorphine present as the free base (unprotonated) form.

In another preferred embodiment, the composition as hereinbefore described comprises buprenorphine present as a protonated salt form.

In a further preferred embodiment, the composition as hereinbefore described further comprises a water soluble polymer is selected from the group consisting of polyethylene glycols (PEG), carboxymethylcelluloses (CMC), polyvinylpyrrolidones (PVP), polyvinylalcohols (PVA) and dextrans.

In a yet further embodiment, there is provided a composition as hereinbefore described wherein the water soluble polymer is a PEG, preferably wherein the PEG has a MW of between 1000 to 10,000.

In a yet further embodiment, there is provided a composition according to any preceding claim which further comprises a nonionic surfactant is selected from the group consisting of Tween 20, Tween 80, poloxamers and phospholipids, preferably wherein the surfactant is one or both of Tween 20 or Tween 80.

In a yet further embodiment, there is provided a composition according to any preceding claim further comprising pharmaceutically acceptable salts or sugars to adjust the tonicity of the composition, and/or preservatives, preferably selected from the group consisting of methylparaben, propylparaben and benzylalcohol.

In a second embodiment of the present invention, there is provided a method of treating a patient for opioid dependence or pain relief comprising administering parenterally and extravascularly a composition substantially as hereinbefore described according to the first embodiment of the present invention.

Preferably, the method according to the second embodiment provides treatment for opioid dependence or pain relief over a period of at least 7 days.

Preferably, the method according to the second embodiment provides treatment for opioid dependence or pain relief over a period of no more than 30 days.

In a particular preference, the method of treating a patient according to the second embodiment provides treatment for opioid dependence or pain relief over a period of at least 7 days and no more than 28 days.

Further preferably, the method of treatment according to the second embodiment provides treatment for opioid dependence or pain relief over a period of at least 10 days and no more than 17 days.

In a further preference of the second embodiment of the invention, there is provided a method of treating a patient comprising a dosage regime of an initial dose plus follow up dosages at a regular time interval of between 7 and 30 days.

In a yet further preference of the second embodiment of the invention, there is provided a method substantially as hereinbefore described which delivers a therapeutically effective dosage of the buprenorphine, metabolite, or prodrug thereof from about 0.1 to about 10 milligrams (mg) or about 1 to about 8 milligrams (mg) per day.

In a yet further preference of the second embodiment of the invention, there is provided a method substantially as hereinbefore described wherein the dosage achieves a therapeutically effective level of the buprenorphine, metabolite, or prodrug thereof, within about one day after administration of the composition; and wherein the therapeutically effective dosage of the buprenorphine, metabolite, or prodrug thereof is delivered for at least about 7 days after administration of the composition, or for at least about 30 days after administration of the composition.

In a third embodiment of the present invention, there is provided a method of forming a composition according to the first embodiment of the invention comprising the steps of:
(a) mixing the water with any further optional component
(b) add the opioid agonist along with a grinding medium
(c) grinding the suspension until the required particle size is achieved.

In a preferred method according to the third embodiment of the present invention, the method further comprises the process of terminally sterilizing the composition, which process comprises the steps of:
(a) fill the composition in pharmaceutically acceptable vials or ampoules and properly seal the vials or ampoules.
(b) terminally sterilizing the vials or ampoules by autoclaving or irradiation (gamma or electron beam).

EXAMPLES

Figure 1:
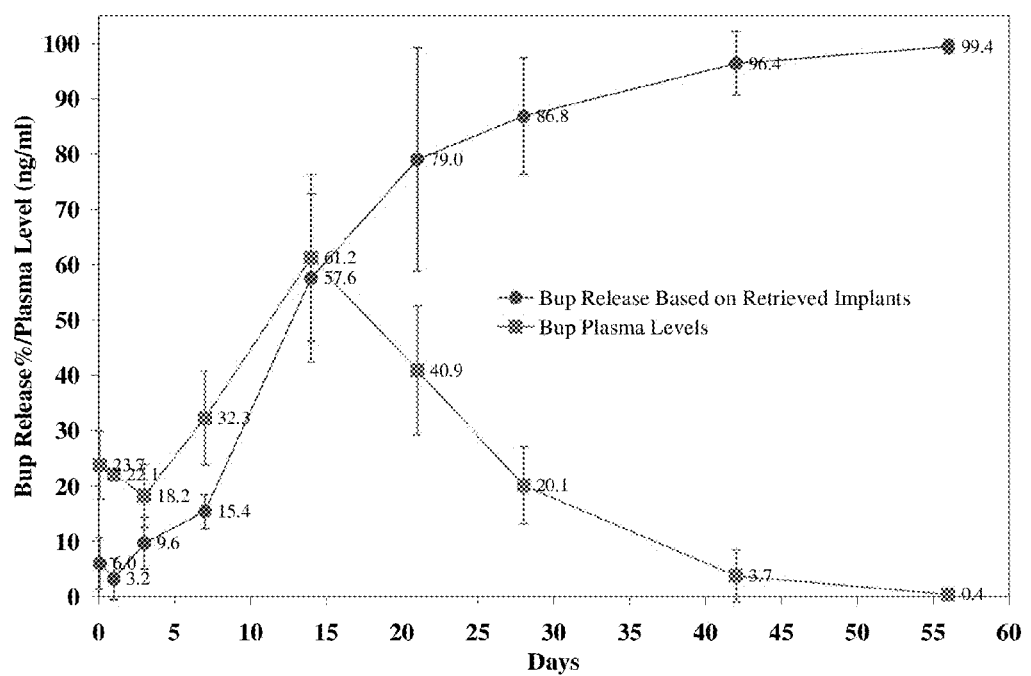
FIG. 1 is a graph showing buprenorphine release and plasma levels after SC injection of buprenorphine free base aqueous suspension in rats.
Figure 2:
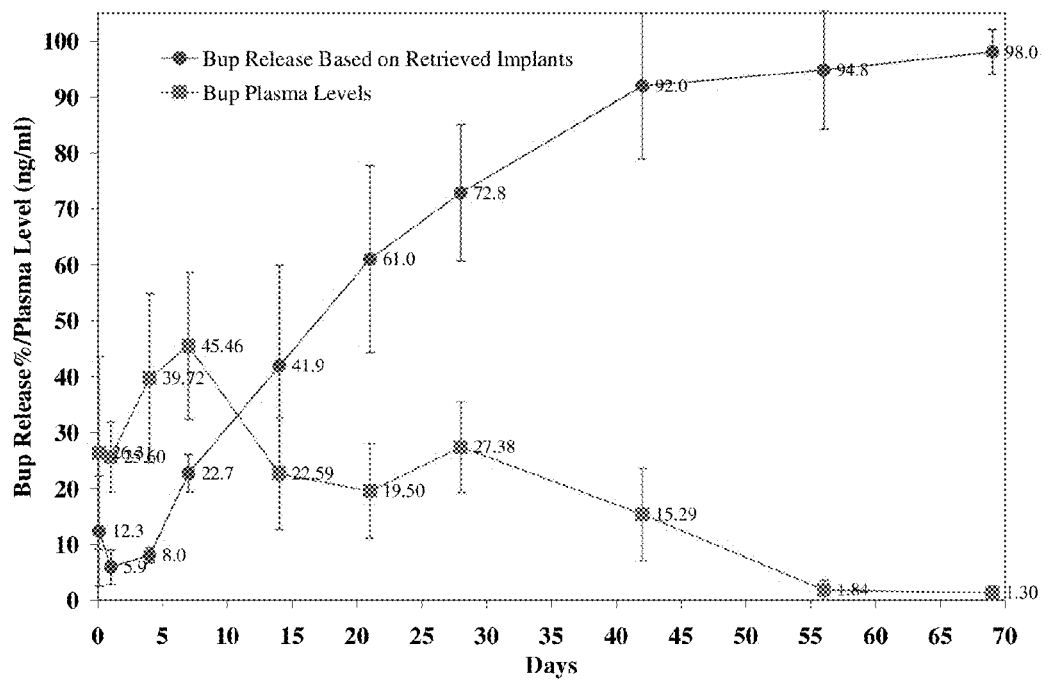
FIG. 2 is a graph showing buprenorphine release and plasma levels after IM injection of buprenorphine free base aqueous suspension in rats.
Figure 3:
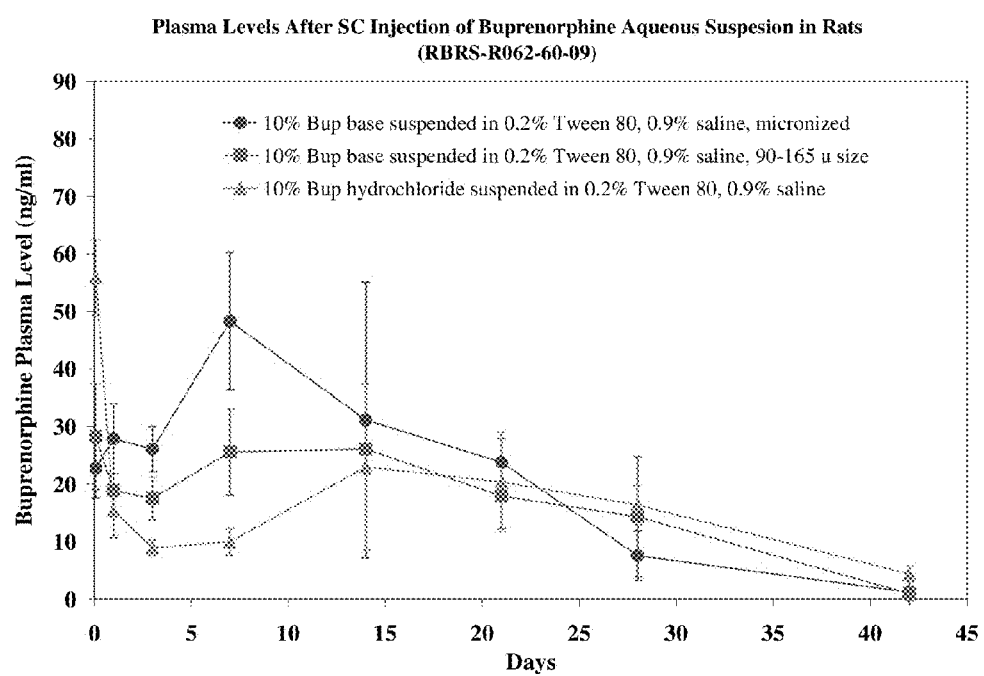
FIG. 3. is a graph showing plasma levels after SC injection of buprenorphine aqueous suspension in rats (RBRS-R062-60-09)
Figure 4:
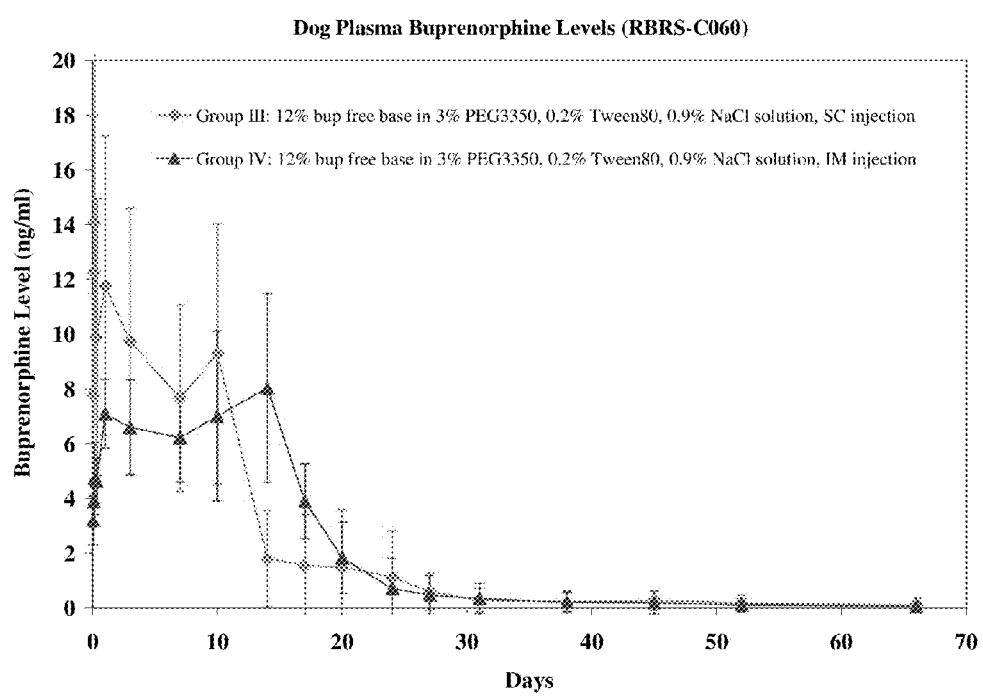
FIG. 4. is a graph showing dog plasma buprenorphine levels (RBRS-0060).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Studies in Rats

Experimental Procedures All rat preclinical studies were conducted in Sprague-Dawley rats. Five rats per Test Article per time point were injected either intramuscularly or subcutaneously under full anesthesia in the dorsal thoracic (DT) region with approximately 200 mg of the Test Article, described above.

During the course of the study, the animals were observed for overt toxicity and any existing test site abnormalities, including redness, bleeding, swelling, discharge, bruising and Test Article extrusion at the injection site were observed and recorded. In addition, injection weights were recorded at administration and body weights were taken and recorded at administration and at termination. At selected time points, five rats per Test Article were anesthetized and bled (about 5 mL) via cardiac puncture. Blood was collected in labeled potassium ethylenediaminetetraacetic acid tubes. The blood was centrifuged for 10 min at 3000 rpm. The plasma fraction was transferred to labeled 5 mL plastic culture tubes and stored at −86° C. The rat plasma samples were analyzed for buprenorphine concentration using a procedure described below. After blood collection, the rat was sacrificed in a carbon dioxide chamber. The injection site was cut open and the drug residue and the surrounding tissues were carefully removed and placed in a scintillation vial. The vials were stored at −20° C. until analysis. The retrieved drug residue/tissue was analyzed for buprenorphine content using the implant analysis method described below.

Buprenorphine Analysis in Rat Plasma Samples

This procedure was based on that described by Li-Heng Pao et al., Journal of Chromatography B, 746(2000), 241-247.

The High Performance Liquid Chromatography had the following conditions: Mobile Phase: 80/20 acetonitrile/5 mM sodium acetate buffer (pH 3.75); flow rate: 1.2 mL/min; autosampler temperature: room temperature; column temperature: 25° C.; detection: fluorescence (excitation at 215 nm and emission at 355 nm); total run time: 14 min; injection volume: 50 µL; column: Phenomenex Luna Silica (2) 250×

4.6 mm, 5 μm; column storage: 100% acetonitrile; approximate retention time for buprenorphine and the internal standard: 7.9 min and 8.7 min.

Implant Extraction/Analysis Procedure

To the vials containing the retrieved drug residue/tissue, exactly 10 mL of the formulation dissolution solution [90/5/5 acetonitrile/glacial acetic acid/water] was added. The vials were then shaken at about 200 rpm at room temperature on the orbital shaker for at least 2 hours. The vials were then centrifuged at 2500 rpm for 10 minutes. After centrifuge, the vials were carefully removed from the centrifuge. A portion of the supernatant from the vial was transferred into a HPLC vial and if necessary, the transferred solution in the vial was further diluted using the formulation dissolution solution to a suitable concentration for HPLC analysis.

The High Performance Liquid Chromatography had the following conditions: Mobile Phase A: 0.065% sodium octanesulfonic acid and 0.1% trifluoroacetic acid in water; Mobile Phase B: 90/10 acetonitrile/0.065% sodium octanesulfonic acid and 0.1% trifluoroacetic acid in water; flow rate: 1.0 ml/min; autosampler temperature: room temperature; column temperature: 30° C.; detection: 285 run (UV); total run time: 21 min; injection volume: 20 μL; column: Phenomenex Luna C18 250×4.6 mm, 5 μm; column storage: 70/30 acetonitrile/water; each sample run according to the following gradient program:

| Time | Mobile Phase A | Mobile Phase B |
|---|---|---|
| 0 | 100% | 0% |
| 2 | 100% | 0% |
| 16 | 20% | 80% |
| 18 | 0% | 100% |
| 20 | 100% | 0% |
| 21 | 100% | 0% | approximate retention time of buprenorphine: 15.4 minutes.

The standard solution preparation is as follows: standard stock solution was made by dissolving approximately 10 mg buprenorphine in 10 mL 1:1 formulation dissolution solution [90/5/5 acetonitrile/glacial acetic acid/water]/H2O. A series standards ranging from 40 ppm to 500 ppm was diluted with water from the standard stock solution.

Studies in Dogs

Experimental Procedures All dog preclinical studies were conducted in male beagles with body weight in the range of 8-12 kg. Six dogs per group were injected subcutaneously in the dorsal thoracic region or intramuscularly in the hind legs at a buprenorphine equivalent dose of 60 mg per dog. Exact injection doses were obtained by weighing the injection syringe before and after each injection. After injection, the dogs were bled periodically via jugular vein into EDTA tubes. Plasma samples were then derived and stored in a −80° C. freezer until analysis. Dogs were weighed once daily on blood collection time points. The test sites were evaluated for any abnormalities including redness, bleeding, swelling, discharge, bruising, and TA extrusion on blood collection days. Dogs were also observed post-administration for signs of overt toxicity throughout the entire study period.

Buprenorphine Analysis in Dog Plasma Samples

Plasma samples from dog studies were analyzed for buprenorphine and norbuprenorphine levels using a LC-MS-MS method through a contract analytical service laboratory. The method was developed and validated by the contract service laboratory. It was a proprietary method that employed a liquid-liquid extraction step followed by LC-MS-MS analysis.

1. Preparation of Buprenorphine Free Base Aqueous Suspension

Exactly 3.0 g PEG3350, 0.2 g Tween 80, and 0.9 g sodium chloride were weighed in a 100-ml volumetric flask. Water was added to dissolve and made up to 100 ml. An aliquot of 17.6 g of this aqueous solution was transferred to a 60-ml glass jar, buprenorphine free base (2.4 g) was then weighed in the jar. The jar was further placed in about 20 half inch size Burundum grinding beads. The jar was closed with a lid and then placed on a jar mill to rotate at 60 rpm at room temperature for 24 hours. The buprenorphine suspension was then filled in 1-ml glass ampoules. The filled ampoules were sealed and autoclaved at 121° C. for 15 minutes. Mean buprenorphine free base particle size [d(0.5)] was measured to be 8.3μ by the Malvern Mastersizer 2000 particle size analyzer.

2. Subcutaneous Injection of Micronized Buprenorphine Free Base Aqueous Suspension in Rats.

Formulation: 10% buprenorphine free base suspension in 3% PEG3350 and 0.2% Tween 80 aqueous solution, micronized, subcutaneous injection of 0.2 ml formulation per rat (20 mg bup per rat) (particle size 3.7μ)

Results:

TABLE 1

Buprenorphine release based on retrieved implant analysis

| Time (Day) | Bup Released % | SD |
|---|---|---|
| 0.083333 | 6.0 | 4.7 |
| 1 | 3.2 | 3.7 |
| 3 | 9.6 | 4.7 |
| 7 | 15.4 | 3.1 |
| 14 | 57.6 | 15.2 |
| 21 | 79.0 | 20.2 |
| 28 | 86.8 | 10.6 |
| 42 | 96.4 | 5.8 |
| 56 | 99.4 | 1.3 |

TABLE 2

Buprenorphine plasma levels

| Time (Day) | Bup Level (ng/ml) | SD |
|---|---|---|
| 0.083333 | 23.7 | 6.2 |
| 1 | 22.1 | 1.1 |
| 3 | 18.2 | 5.7 |
| 7 | 32.3 | 8.5 |
| 14 | 61.2 | 15.0 |
| 21 | 40.9 | 11.7 |
| 28 | 20.1 | 6.9 |
| 42 | 3.7 | 4.7 |
| 56 | 0.4 | 0.8 |

3. Intramuscular Injection of Micronized Buprenorphine Free Base Aqueous Suspension in Rats.

Formulation: 13.3% buprenorphine free base suspension in 3% PEG3350, 0.2% Tween 80, and 0.9% sodium chloride aqueous solution, micronized, intramuscular injection of 0.15 ml formulation per rat (20 mg bup per rat) (particle size 10.5μ)

Results:

TABLE 3

Buprenorphine release based on retrieved implant analysis

| Time (day) | Bup Released % | SD |
|---|---|---|
| 0.083333 | 12.3 | 9.9 |
| 1 | 5.9 | 3.1 |
| 4 | 8.0 | 1.3 |
| 7 | 22.7 | 3.4 |
| 14 | 41.9 | 18.0 |
| 21 | 61.0 | 16.7 |
| 28 | 72.8 | 12.2 |
| 42 | 92.0 | 13.0 |
| 56 | 94.8 | 10.5 |
| 69 | 98.0 | 4.0 |

TABLE 4

Buprenorphine plasma levels

| Time (Day) | Bup Level (ng/ml) | SD |
|---|---|---|
| 0.083333 | 26.3 | 17.2 |
| 1 | 25.6 | 6.3 |
| 4 | 39.7 | 15.1 |
| 7 | 45.5 | 13.2 |
| 14 | 22.6 | 10.0 |
| 21 | 19.5 | 8.5 |
| 28 | 27.4 | 8.2 |
| 42 | 15.3 | 8.3 |
| 56 | 1.8 | 1.7 |
| 69 | 1.3 | 1.2 |

4. Subcutaneous Injection of Micronized/Larger Particle Size Buprenorphine Free Base Aqueous Suspensions as Well as Buprenorphine Hydrochloride Suspension in Rats) (Particle Size Group I=4.7µ, Group II=40.3µ)

Formulation:

Group I: 10% buprenorphine free base suspension in 0.2% Tween 80 and 0.9% sodium chloride aqueous solution, micronized, subcutaneous injection of 0.20 ml formulation per rat (20 mg bup per rat)

Group II: 10% buprenorphine free base suspension in 0.2% Tween 80 and 0.9% sodium chloride aqueous solution, subcutaneous injection of 0.20 ml formulation per rat (20 mg bup per rat)

Group III: 10% buprenorphine hydrochloride suspension in 0.2% Tween 80 and 0.9% sodium chloride aqueous solution, micronized, subcutaneous injection of 0.20 ml formulation per rat (20 mg bup per rat)

Results:

TABLE 5

Buprenorphine release based on retrieved implant analysis

| Time (Day) | Group I | SD | Group II | SD | Group III | SD |
|---|---|---|---|---|---|---|
| 0.083333 | 0.1 | 4.5 | 19.6 | 7.8 | 13.9 | 8.5 |
| 1 | 3.9 | 2.1 | 1.4 | 18.6 | 41.4 | 3.7 |
| 3 | 5.1 | 1.2 | 15.4 | 31.4 | 20.1 | 10.3 |
| 7 | 20.5 | 4.4 | 2.6 | 10.4 | 26.3 | 5.4 |
| 14 | 49.5 | 18.0 | 37.7 | 33.5 | 36.7 | 8.7 |
| 21 | 75.0 | 17.1 | 55.9 | 31.2 | 49.6 | 15.5 |
| 28 | 93.8 | 6.6 | 78.5 | 22.3 | 70.7 | 16.6 |
| 42 | 99.9 | 0.1 | 96.6 | 2.1 | 77.0 | 21.8 |

TABLE 6

Buprenorphine plasma levels

| Time (Day) | Group I | SD | Group II | SD | Group III | SD |
|---|---|---|---|---|---|---|
| 0.083333 | 22.7 | 5.1 | 28.2 | 9.2 | 55.9 | 6.6 |
| 1 | 27.9 | 6.1 | 18.9 | 8.3 | 15.4 | 4.3 |
| 3 | 26.1 | 3.9 | 17.5 | 3.7 | 8.9 | 1.4 |
| 7 | 48.3 | 11.9 | 25.6 | 7.5 | 9.9 | 2.3 |
| 14 | 31.1 | 23.9 | 26.1 | 4.4 | 23.0 | 14.4 |
| 21 | 23.7 | 4.2 | 17.9 | 5.7 | 20.3 | 8.7 |
| 28 | 7.6 | 4.3 | 14.3 | 10.4 | 16.4 | 3.4 |
| 42 | 1.2 | 2.7 | 1.0 | 1.3 | 4.3 | 1.4 |

5. Subcutaneous and Intramuscular Injections of Micronized Buprenorphine Free Base Aqueous Suspension in Dogs)

Formulation: 12% buprenorphine free base suspension in 3% PEG3350, 0.2% Tween 80, and 0.9% sodium chloride aqueous solution, micronized, subcutaneous and intramuscular injection of 0.5 ml formulation per dog (60 mg bup per dog) (particle size 8.3µ)

Results:

TABLE 7

Buprenorphine plasma levels after SC injection of bup suspension (Group III)

| Day | BDT8 | TWL5 | SPT8 | TAT8 | WHV8 | XPT8 | Mean | SD |
|---|---|---|---|---|---|---|---|---|
| −4 | * | 0.156 | * | * | * | * | | |
| 1 hour | 3.44 | 5.58 | 13.3 | 7.66 | 10.9 | 5.99 | 7.81 | 3.66 |
| 2 hour | 5.45 | 8.06 | 19.6 | 16.1 | 16.1 | 8.4 | 12.29 | 5.70 |
| 4 hour | 6.04 | 10.1 | 18.5 | 19.5 | 21 | 9.28 | 14.07 | 6.33 |
| 8 hour | 3.51 | 11.9 | 10.6 | 12.6 | 16.5 | 4.25 | 9.89 | 5.06 |
| 1 | 6.64 | 9.2 | 8.3 | 11.5 | 21.9 | 13.1 | 11.77 | 5.47 |
| 3 | 2.84 | 5.8 | 10.9 | 16.1 | 13.4 | 9.4 | 9.74 | 4.87 |
| 7 | 2.79 | 4.1 | 8.62 | 11 | 8.93 | 10.5 | 7.66 | 3.41 |
| 10 | 7.07 | 2.45 | 6.68 | 11.5 | 15.7 | 12.3 | 9.28 | 4.77 |
| 14 | 5.08 | 1.43 | 1.82 | 0.723 | 0 | 1.78 | 1.81 | 1.75 |
| 17 | 5.2 | 1.41 | 1.44 | 0.362 | 0.104 | 0.754 | 1.55 | 1.87 |
| 20 | 5.64 | 1.37 | 1.16 | 0.295 | * | 0.456 | 1.49 | 2.10 |
| 24 | 4.4 | 1.33 | 0.75 | 0.272 | * | * | 1.13 | 1.68 |
| 27 | 1.63 | 1.14 | 0.651 | 0.176 | * | * | 0.60 | 0.67 |
| 31 | 0.13 | 1.06 | 0.489 | * | * | * | 0.28 | 0.43 |
| 38 | * | 0.968 | 0.322 | * | * | * | 0.22 | 0.39 |
| 45 | 0.389 | 0.894 | 0.354 | | | | 0.27 | 0.35 |
| 52 | * | 0.767 | 0.232 | | | | 0.17 | 0.31 |
| 66 | * | 0.618 | * | | | | 0.10 | 0.25 |

TABLE 8

Buprenorphine plasma levels after IM injection of bup suspension (Group IV)

| Day | FLV8 | ITV8 | TEV8 | TQT8 | WOT8 | YHT8 | Mean | SD |
|---|---|---|---|---|---|---|---|---|
| −4 | 0.267 | * | * | * | 2.42 | * | | |
| 1 hour | 2.72 | 4.1 | 1.99 | 4.37 | 2.84 | 3.17 | 3.20 | 0.89 |
| 2 hour | 3.73 | 5.38 | 3.18 | 4.15 | 2.99 | 3.87 | 3.88 | 0.85 |
| 4 hour | 4.23 | 6.36 | 2.91 | 5.62 | 3.7 | 5.57 | 4.73 | 1.32 |
| 8 hour | 4.54 | 4.41 | 3.96 | 6.13 | 3.91 | 4.9 | 4.64 | 0.82 |
| 1 | 7.14 | 8.7 | 5.61 | 8.22 | 5.71 | 7.18 | 7.09 | 1.26 |
| 3 | 8.07 | 8.63 | 4.31 | 7.3 | 4.85 | 6.4 | 6.59 | 1.74 |
| 7 | 7.54 | 7.63 | 3.53 | 6.81 | 4.98 | 6.8 | 6.22 | 1.62 |
| 10 | 5.93 | 4.75 | 4.67 | 12.7 | 8.42 | 5.58 | 7.01 | 3.10 |
| 14 | 10.2 | 4.37 | 4.7 | 13.2 | 9.17 | 6.56 | 8.03 | 3.45 |
| 17 | 4.11 | 3.74 | 4.14 | 1.34 | 4.81 | 5.26 | 3.90 | 1.37 |
| 20 | 1.53 | 2.81 | 3.51 | 0.227 | 2.4 | 0.506 | 1.83 | 1.31 |
| 24 | * | 1.92 | 2.32 | * | * | * | 0.71 | 1.10 |
| 27 | * | 1.26 | 1.52 | * | * | * | 0.46 | 0.72 |
| 31 | * | 1.2 | 0.882 | * | * | * | 0.35 | 0.55 |
| 38 | * | 0.797 | 0.511 | * | * | * | 0.22 | 0.35 |
| 45 | * | 1.03 | 0.159 | * | * | * | 0.20 | 0.41 |
| 52 | | 0.598 | * | | | | 0.10 | 0.24 |
| 66 | | 0.355 | * | | | | 0.06 | 0.14 |

{* = BLQ < 0.01}

The invention claimed is:

1. An injectable pharmaceutical composition comprising:
  (a) 10 wt % to 20 wt % buprenorphine free base having an average particle size of less than 20 µm; and
  (b) an aqueous solution comprising polyoxyethylene (20) sorbitan monolaurate, polyoxyethylene (20) sorbitan monooleate, or a combination thereof; and a polyethylene glycol polymer;
wherein the buprenorphine free base is suspended in the aqueous solution, and wherein the composition does not comprise one or both of a polylactide and polyglycolide polymer.

2. The composition of claim 1, wherein the buprenorphine free base has an average particle size of less than 10 µm.

3. The composition of claim 1, wherein the aqueous solution comprises polyoxyethylene (20) sorbitan monolaurate and a polyethylene glycol polymer having a molecular weight between 1,000 and 10,000.

4. The composition of claim 1, wherein the aqueous solution comprises polyoxyethylene (20) sorbitan monooleate and a polyethylene glycol polymer having a molecular weight between 1,000 and 10,000.

5. The composition of claim 1, wherein the aqueous solution comprises polyoxyethylene (20) sorbitan monolaurate, polyoxyethylene (20) sorbitan monooleate, and a polyethylene glycol polymer having a molecular weight between 1,000 and 10,000.

6. The composition of claim 1, wherein the polyethylene glycol polymer has a molecular weight between 1,000 and 10,000.

7. The composition of claim 1, wherein the aqueous solution further comprising a pharmaceutically acceptable salt, a pharmaceutically acceptable sugar, a preservative, or a combination of two or more thereof.

8. An injectable pharmaceutical composition comprising
  (a) about 5 wt % to about 20 wt % of buprenorphine free base having an average particle size of less than 50 µm; and
  (b) an aqueous solution comprising (i) polyoxyethylene (20) sorbitan monolaurate, polyoxyethylene (20) sorbitan monooleate, a poloxamer, a phospholipid, or a combination thereof, and (ii) a polyethylene glycol polymer, a carboxymethylcellulose, a polyvinylpyrrolidone, a polyvinylalcohol, or a dextran;
wherein the buprenorphine free base is suspended in the aqueous solution, and wherein the composition does not comprise one or both of a polylactide and polyglycolide polymer.

9. The composition of claim 8 comprising about 10 wt % to about 20 wt % buprenorphine free base.

10. The composition of claim 8, wherein the buprenorphine free base has an average particle size of less than 20 µm.

11. The composition of claim 8, wherein the aqueous solution comprises (i) polyoxyethylene (20) sorbitan monolaurate, polyoxyethylene (20) sorbitan monooleate, or a combination thereof, and (ii) a polyethylene glycol polymer.

12. The composition of claim 8, wherein the aqueous solution further comprises a pharmaceutically acceptable salt, a pharmaceutically acceptable sugar, a preservative, or a combination of two or more thereof.

13. A pharmaceutical composition comprising buprenorphine or a pharmaceutically acceptable salt thereof, having an average particle size of less than 200 µm, suspended in an aqueous solution comprising a nonionic surfactant and a water-soluble polymer.

14. The composition of claim 13, wherein the buprenorphine or the pharmaceutically acceptable salt thereof is present in an amount of about 10 wt % to about 20 wt %.

15. The composition of claim 13, wherein the buprenorphine or the pharmaceutically acceptable salt thereof has an average particle size of is less than 100 µm.

16. The composition of claim 13, wherein the buprenorphine is present as the free base (unprotonated) form.

17. The composition of claim 13, wherein the buprenorphine is present as a pharmaceutically acceptable salt.

18. The composition of claim 13, wherein the aqueous solution further comprises a pharmaceutically acceptable salt, a pharmaceutically acceptable sugar, a preservative, or a combination of two or more thereof.

19. The composition of claim 13, wherein the nonionic surfactant is polyoxyethylene (20) sorbitan monolaurate, polyoxyethylene (20) sorbitan monooleate, a poloxamer, a phospholipid, or a combination thereof.

20. The composition of claim 13, wherein the water-soluble polymer is a polyethylene glycol polymer, a carboxymethylcellulose, a polyvinylpyrrolidone, a polyvinylalcohol, a dextran, or a combination of two or more thereof.

* * * * *